United States Patent [19]

Neumann et al.

[11] Patent Number: 4,847,376

[45] Date of Patent: Jul. 11, 1989

[54] LIPASE SUBSTRATES

[75] Inventors: Ulrich Neumann, Peissenberg; Martina Junius, Bernried; Hans-Georg Batz, Tutzing, all of Fed. Rep. of Germany

[73] Assignee: Boehringer Mannheim GmbH, Mannheim, Fed. Rep. of Germany

[21] Appl. No.: 858,349

[22] Filed: May 1, 1986

[30] Foreign Application Priority Data

May 3, 1985 [DE] Fed. Rep. of Germany ....... 3516001

[51] Int. Cl.$^4$ .......................................... C07D 265/38
[52] U.S. Cl. ..................... 544/102; 260/405; 544/104; 558/251; 558/255; 560/146; 560/171; 548/407; 549/11; 549/29
[58] Field of Search ............... 544/102, 104; 260/405; 558/251, 255; 560/146, 171; 548/407; 549/11, 29

[56] References Cited

U.S. PATENT DOCUMENTS 4,667,032 5/1987 Lau et al. ...................... 544/102 X

FOREIGN PATENT DOCUMENTS 3342106 6/1984 Fed. Rep. of Germany .

Primary Examiner—Richard L. Raymond
Attorney, Agent, or Firm—Felfe & Lynch

[57] ABSTRACT

The present invention provides a lipase substrate of the general formula:

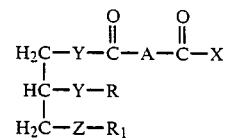

wherein A is an alkylene or alkenylene radical containing up to 16 carbon atoms, R and $R_1$, which can be the same or different, each signify an alkyl, alkenyl or acyl radical containing up to 20 carbon atoms or an optionally alkyl-substituted aryl or aralkyl radical containing up to 8 carbon atoms in the alkyl moiety and wherein one of R and $R_1$ can also be a hydrogen atom, X is the residue of an aromatic hydroxy or thiol compound, and each Y and Z, independently from each other, is —S— or —O—, Z also —$CH_2$—.

The present invention also provides a process and a reagent for the optical determination of lipase.

7 Claims, No Drawings

LIPASE SUBSTRATES

The present invention is concerned with new lipase substrates and with a process and reagent for the optical determination of lipase.

Lipase (triacylglycerol acyl hydrolase EC 3.1.1.3) hydrolyses emulsified triglycerides of long-chained fatty acids on the boundary surface between oil droplets and aqueous phase. In the case of certain diseases, such as acute pancreatitis or carcinoma of the pancreas, the normally very low lipase concentration in the serum is increased and the determination of the lipase activity is, therefore, of considerable diagnostic importance. Consequently, the determination of lipase is of considerable importance not only for clinical chemistry but also for biochemistry, pharmaceutical chemistry and foodstuff chemistry.

Several lipase measurement methods are already known. Thus, the liberated acid can be determined titrimetrically with lye but this method is subject to disturbances and is not especially specific. Furthermore, a photometric determination in the UV is known. Thus, Federal Republic of Germany Patent Specification No. 33 42 106 describes the use of a mono- or diglyceride of a higher fatty acid, in combination with a non-ionic tenside, as a substrate for the UV determination. However, UV tests require a relatively laborious measurement apparatus and do not readily permit the recognition of possible disturbances, such as apparatus defects and exhaustion of the reagent. Therefore, there is a need for a colour test which can be carried out with a simple apparatus and can be directly visually monitored.

There is already known the colour test of Kurooka which uses a dimercaptopropanol triester as substrate, together with a dithiobisnitrobenzoic acid as chromogen, an esterase inhibitor and a lipase activator. However, this process is not very accurate (J. Clin. Chem. Clin. Biochem. 20, 537-552/1982). Furthermore, a process is known which uses trilinolein as substrate and lipoxygenase as adjuvant system, in which, in a subsequent colour reaction, ferrous iron is oxidised to ferric iron by fatty acid hydroperoxide and is detected as ferric thiocyanate. However, this method does not give dependable results (J. Clin. Chem. Biochem. 20, 745-752/1982).

A turbidity determination is also known which, however, only has a relatively low sensitivity.

Therefore, it is an object of the present invention to provide a colour test for the determination of lipase which does not display the disadvantages of the known colour tests, provides exact results, is simple to use, possesses a high sensitivity and only displays a small lag phase so that adaptation to various automatic analysis systems is not difficult.

Thus, according to the present invention, there is provided a lipase substrate of the general formula:

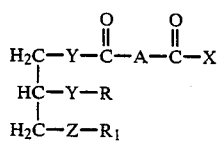

wherein A is an alkylene or alkenylene radical containing up to 16 carbon atoms, R and $R_1$, which can be the same or different, each signify an alkyl, alkenyl or acyl radical containing up to 20 carbon atoms or an optionally alkyl-substituted aryl or aralkyl radical containing up to 8 carbon atoms in the alkyl moiety and wherein one if R and $R_1$ can also be a hydrogen atom, X is the residue of an aromatic hydroxy or thiol compound, and each Y and Z, independently from each other, is —S— or —O—, Z also —$CH_2$—.

By means of the action of lipase, the lipase substrate according to the present invention is split with liberation of the aromatic hydroxy or thiol compound corresponding to the radical X which is either directly determined optically or is coupled with an appropriate chromophore and the colour thereby formed is measured.

R and/or $R_1$ preferably contain 6 to 18 carbon atoms and especially preferably 8 to 12 carbon atoms. Because of their insensitivity to hydrolysis, for R and $R_1$, alkyl radicals are especially preferred to acyl radicals. Surprisingly, compounds in which R and $R_1$ are alkyl, alkenyl or aralkyl radicals prove to be good lipase substrates, although natural triglycerides contain acyl radicals.

Examples of R and/or $R_1$ include methyl, ethyl, propyl, butyl, pentyl, hexyl, heptyl, octyl, nonyl, decyl, undecyl, dodecyl, tetradecyl, hexadecyl and octadecyl radicals as alkyl radicals, as well as the corresponding acyl radicals, such as acetyl, propionyl, butyryl, valeryl, capronyl, capryl, caprinyl, lauryl, myristyl, palmityl and stearyl radicals, and also oleyl, crotonyl, linolyl, phenyl, benzyl and octylphenyl radicals.

The lipase substrate according to the present invention also contains the residue of a dicarboxylic acid of the general formula COOH—A—COOH, in which A preferably contains 3 to 7 carbon atoms. Examples for acids from which A is derived include malonic acid, succinic acid, glutaric acid, adipic acid, pimelic acid, suberic acid, azelaic acid, sebacic acid, nonane-dicarboxylic acid, decane-dicarboxylic acid and undecane-dicarboxylic acid. The acids from glutaric acid to azelaic acid, which correspond to A containing 3 to 7 carbon atoms, are, as mentioned above, preferred.

X can be the residue of an aromatic hydroxy or thiol compound which either represents a chromophore or is first converted into a coloured material by a subsequent reaction. Typical examples of such aromatic hydroxy and thiol compounds include phenol, thiophenol, naphthol, thionaphthol and derivatives thereof, as well as per se chromogenic compounds, such as resorufin, chlorophenol red, indoxyl and thiofluorescein residues. An exhaustive enumeration of suitable hydroxy or thiol compounds is, because of their large number, not possible but the directly chromophoric aromatic hydroxy and thiol compounds and those which are convertible into chromophores are well known.

Chromophores with little polarity and which are lipophilic are preferred. But the solubility in water should still be maintained.

The lipophilic character of the said chromophores can positively be influenced by appropriate substitution, as for instance with alkyl groups. Suitable substituents for the resorufin residue are, amongst others, the methyl, dimethyl and ethyl groups, as well as the substitution with bromine.

The compounds according to the invention are new. They possess a centre of assymetry and are, therefore, optically active. As lipase substrate, there can be used not only the racemates obtained in the case of the usual methods of preparation but also the optical isomers.

The preparation of the lipase substrates according to the present invention can take place by known methods. Thus, suitable processes for the syntheses of the 1,2-O-diether- and 1,2-diacyl-glycerol compounds are described, for example, in Methods in Enzymology, 98, 623/1983 and Oleagineux 23, 185/1968. The synthesis of alkane-diol derivatives is, for instance, disclosed in Can. J. Biochem. 46 (1968) 69.

From the 1,2-O-diether- and 1,2-diacyl-glycerol compounds are then obtained the corresponding glycerodicarboxylic acid monoesters by reaction with the corresponding dicarboxylic acid anhydrides in an anhydrous medium, such as chloroform/pyridine. Suitable methods for the preparation of the dicarboxylic acid anhydrides are described in Houben-Weyl-Muller "Methoden der organischen Chemie", Volume IV/4, page 786.

The esterification of the monoester with the aromatic hydroxy or thiol compound, from which the residue X is derived, can be carried out, for example, by direct reaction of the dicarboxylic acid monoester with the aromatic alcohol or thiol in the presence of a water-removing agent, such as dicyclohexylcarbodiimide. Alternatively, the dicarboxylic acid monoester is first converted into an activated ester, for example into the hydroxysuccinimide ester or the imidazolide, and the activated ester is then reacted with the aromatic alcohol or thiol.

In the same way, it is also possible first to prepare a monoester of the dicarboxylic acid with the aromatic alcohol or thiol, for example adipic acid mononitrophenyl ester or glutaric acid monophenyl ester, and then to esterify this with a 1,2-O-dialkyl- or -diacyl-glycerol, for example via the intermediate formation of an acid chloride, anhydride or activated ester. The preparation of the dicarboxylic acid monoester with the aromatic alcohol or thiol can, for example, take place from the acid anhydride and the aromatic compound in the mole ratio of 1:1 or from the dicarboxylic acid and the aromatic compound in the mole ratio of 2:1 or from a dicarboxylic acid monoester with a protective group which is easily split off and the aromatic compound. A suitable method is described, for example, in Arch. Pharm. 287, 514/1954.

Alternatively, the 1,2-O-dialkyl- or 1,2-O-diacyl-glycero-dicarboxylic acid monoester can also be prepared by first preparing a dicarboxylic acid monoester from the dicarboxylic acid and an alcohol which is easily split off, for example benzyl- or 2,2,2-trichloroethyl alcohol, and the acid so obtained is then esterified with the mentioned dialkyl- or diacyl-glycerol. Subsequently, the protective group is removed and the reaction with the aromatic alcohol or thiol is carried out as described above.

A further preparation method consists in first reacting a protected glycerol, such as 1,2-isopropyl-idene-glycerol, with a dicarboxylic acid monoester with the formation of the corresponding protected glycero-3-dicarboxylic acid diester, the protective group of the glycerol is then removed and the liberated hydroxyl groups are alkylated or acylated. Finally, the monoester group (carboxyl protective group) originally present is split off, followed by reaction with the aromatic alcohol or thiol.

The above-described preparations of the substrates according to the present invention is not exhaustive and a number of further per se known methods is available which enable the ready preparation of the compounds according to the present invention. From the racemic products obtained according to the abovedescribed processes there can be obtained, if desired, the pure optical isomers according to known separation processes. However, the isomers can also be obtained by stereospecific syntheses according to per se known processes.

The process according to the present invention for the optical determination of lipase comprises subjecting a lipase substrate according to the present invention to the action of a lipase-containing sample and optically determining the amount of liberated aromatic hydroxy or thiol compound directly or, after coupling with an appropriate chromogen, determining the colour formed therefrom.

An especial feature of this process is the fact that it does not require adjuvant enzymes or esterase inhibitors such as are frequently required in the case of the known methods. Such additives are not only expensive but frequently also not very stable. Therefor, a special advantage of the present invention is the fact that it also provides a simple and well-storable reagent for the optical determination of lipase which, besides a lipase substrate according to the present invention and buffer substance, also contains a surface-active agent, such as especially a bile acid salt, colipase, a chromogenic coupler and/or a salt, such as sodium chloride. Furthermore, the reagent preferably also contains urea, a preserving agent and/or an activator.

According to a preferred composition, this reagent contains 0.05 to 10 mg./ml. substrate,
2 to 50 mg./ml. desoxycholate,
0.001 to 0.01 mg./ml. colipase,
1 to 100 mg./ml. urea,
0.1 to 10 mg./ml. sodium chloride and
1 to 50 mg./ml. buffer substance,
in each case referred to the solution ready for use in the test.

As bile acids, there can be used the known surface-active bile acids, such as cholic acid, taurocholic acid, desoxycholic acid, taurodesoxycholic acid, glycodesoxycholic acid and the alkali metal salts thereof and especially the sodium salt. The preferred amount thereof is from 2 to 50 mg./ml.

A further important component of the reagent according to the present invention is colipase, a colipase free from impurities being especially preferred. The preferred amount thereof is from 0.001 to 0.01 mg./ml.

Furthermore, the reagent according to the present invention can contain urea, preferably in an amount of from 1 to 100 mg./ml.

As buffer substance, there can be used all known buffers which are able, in the reagent according to the present invention, to adjust a pH value of from 6.0 to 10.5, the preferred pH value range being from 7.0 to 9.5. Examples of appropriate buffers include diethanolamine buffer, triethanolamine buffer, tris buffer and Good buffers, such as hepes buffer (appropriate for addition before lyophilisation), taps buffer, CHES buffer (2-(cyclohexylamino)-ethanesulphonic acid) and bicine, tris buffer being especially preferred. The preferred amount of buffer substance is from 1 to 50 mg./ml.

As salts, there can be used, for example, alkali metal, alkaline earth metal and ammonium salts, preferably in concentrations of from 0.1 to 10 mg./ml.

As preserving agents, in the scope of the present invention, those are used which do not impair the enzymatic activity of the lipase to be determined. Especially preferred are the alkali metal azides and particularly sodium azide. Other preserving agents, for example thiozide and other sulphur-containing preserving agents, can, however, also be used. The preferred amount of preserving agent is from 0.001 to 2 mg./ml.

As activators, there can be used alkaline earth metal ions and preferably calcium ions. Since these form insoluble compounds with desoxycholic acid, in the case of the presence of calcium, as bile acid tauro-desoxycholic acid is preferred since this permits higher calcium concentrations in the range of from 1 to 5 mMole.

If the reagent according to the present invention is used in a dry or concentrated form intended for dilution to give the final composition, then it contains the mentioned substances in corresponding amount ratios, as well as preferably a protective colloid.

As protective colloids, there can be used those substances known for this purpose, such as polyhydroxy compounds, serum albumin, polyvinylpyrrolidone, solid polyethylene oxides and the like. Polyhydroxy compounds are preferred and especially monomeric and polymeric pentoses or hexoses containing up to 10 pentose or hexose units in the molecule and/or polyethylene glycols which are solid at ambient temperature. Preferred examples of appropriate polyhydroxy compounds include mannitol and similar sugar alcohols, oligosaccharides of glucose, mannose, maltoheptaose, polyethylene glycols with an average molecular weight of from 3500 to 7000 and the like. Other protective colloids which can be used include, for example, amino acids, such as alanine, vegetable gums, such as gum arabic and the like. The preferred amount of protective colloid or of a mixture of protective colloids is from 20 to 90% by weight. A mixture of sugar alcohol and polyalkylene glycol has proved to be especially useful.

The reagent according to the present invention can also be impregnated on to an appropriate carrier material. For this purpose, there can be used not only an absorbent carrier material but also a swellable, soluble, film-forming carrier material. In this form, the reagent according to the present invention makes possible the production of test strips which can be evaluated directly visually or by means of appropriate measurement apparatus.

The colour test according to the present invention for the determination of lipase provides very precise results in the case of high sensitivity. It is very easy to handle and can also be used for test strips. Since it displays only a very small or even no lag phase, it can readily be adapted to various automatic analysis systems.

The determination itself can be carried out not only as an end point determination but also kinetically. In comparison with many known processes, a kinetic carrying out provides the advantage that neither a stopping nor a shaking out of the reaction product formed has to be carried out.

The following Examples are given for the purpose of illustrating the present invention:

EXAMPLE 1

(a) 1,2-O-Dihexyl-rac-glycero-3-glutaric acid monoester

To a solution of 3.3 g. (11.5 mM) 1,2-O-dihexylglycerol in 30 ml. chloroform are successively added 2.5 ml. pyridine, a spatula tip of 4-dimethylaminopyridine and 2.6 g. (23 mM) glutaric acid anhydride. The mixture is heated under reflux for 10 hours and, after cooling, diluted with 200 ml. chloroform. The chloroform phase is shaken with 1N hydrochloric acid and dried. After filtering off the drying agent, the solvent is stripped off and the residue is purified over a silica gel column (eluent: ethyl acetate/petroleum ether 1:1 v/v).

TLC: $R_f$: 0.45 (ethyl acetate/petroleum ether 1:2+1% glacial acetic acid)

1,2-O-Dihexyl-rac-glycero-3-glutaric acid resorufin ester (b) 1.4 g. (3.7 mM) of 1(a) are dissolved in 20 ml. chloroform and, with ice cooling, mixed dropwise with 2 ml. (23.3 mM) oxalyl chloride. The ice bath is removed and the solution is stirred for 12 hours at ambient temperature. Subsequently, the solvent is stripped off and the residue is taken up in toluene and again evaporated. The oil so obtained is used without further purification.

(c) 0.8 g. (3.7 mM) Resorufin is slurried in 40 ml. dimethylformamide, with the addition of 1.1 ml. pyridine and a spatula tip of 4-dimethylaminopyridine. A solution of 1(b) in 20 ml. dimethylformamide is added dropwise hereto. After stirring for 1 to 2 days at ambient temperature, the reaction mixture is filtered and the solvent is stripped off. The residue is taken up in ethyl acetate, insoluble components are filtered off and the filtrate is shaken with 1N hydrochloric acid and then with water. After drying the organic phase and distilling off the solvent, an oily residue is obtained which is purified by column chromatography on silica gel (eluent: ethyl acetate/petroleum ether 1:1 v/v).

TLC: $R_f$: 0.70 (ethyl acetate/hexane 1:1)

EXAMPLE 2

(a) 1,2-O-Dioctyl-rac-glycero-3-glutaric acid monoester

Preparation analogous to Example 1(a) from 13 g. (41 mM) 1,2-O-dioctylglycerol, 150 ml. chloroform, 10 ml. pyridine and 6.8 g. (59.5 mM) glutaric acid anhydride. Yield: 6.5 g. (37%).

TLC: $R_f$: 0.31 (ethyl acetate/petroleum ether 1:1 v/v).

1,2-O-Dioctyl-rac-glycero-3-glutaric acid resorufin ester (b) Preparation analogous to Example 1(b) from 2 g. (4.5 mM) 2(a).

(c) 0.96 g. (4.5 mM) Resorufin are dissolved in 50 ml. chloroform, with the addition of 0.75 ml. (5 mM) 1,8-diazabicyclo-(5,4,0)-undec-7-ene and 0.1 g. 4-dimethylaminopyridine. To this is added dropwise a solution of 2(b) in 20 ml. chloroform. After stirring for 1 to 2 days at ambient temperature, the reaction mixture is filtered and the solvent is stripped off. Working up analogous to Example 1(c).

TLC: $R_f$: 0.66 (ethyl acetate/hexane 1:1 v/v).

EXAMPLE 3

(a) 1,2-O-Dioctyl-rac-glycero-3-pimelic acid monoester

Preparation analogous to Example 1(a) from 3.2 g. (10 mM) 1,2-O-dioctylglycerol and 2.1 g. (15 mM) pimelic acid anhydride.

TLC: $R_f$: 0.61 (ethyl/petroleum ether 1:1 v/v)
IR (cm$^{-1}$): (film): 1740, 1710

1,2-O-dioctyl-rac-glycero-3-pimelic acid resorufin ester (b) Preparation analogous to Example 1(b) from 2.2 g. (4.7 mM) 3(a).

(c) Preparation analogous to Example 2(c) from 1 g. (4.7 mM) resorufin, 0.7 ml. 1,8-diazabicyclo-(5,4,0)-undec-7-ene and 3(b).

TLC: $R_f$: 0.78 (ethyl acetate/hexane 1:2 v/v).

EXAMPLE 4

(a) 1,2-O-Dioctyl-rac-glycero-3-azelaic acid monoester

Preparation analogous to Example 1(a) from 6.3 g. (20 mM) 1,2-O-dioctylglycerol, 80 ml. chloroform, 5 ml. pyridine and 5.2 g. (30 mM) azelaic acid anhydride.

1,2-O-dioctyl-rac-glycero-3-azelaic acid resorufin ester (b) Preparation analogous to Example 1(b) from 3.2 g. (6.5 mM) 4(a) and 3 ml. oxalyl chloride.

(c) Preparation analogous to Example 2(c) from 1.4 g. (6.5 mM) resorufin, 65 ml. chloroform, 1.1 ml. 1,8-diazabicyclo-(5,4,0)-undec-7-ene and 4(b).

TLC: $R_f$: 0.86 (ethyl acetate/hexane 1:2 v/v).
IR (cm$^{-1}$): (film) 1762, 1736.

EXAMPLE 5

(a) 1,2-O-Didecyl-rac-glycero-3-glutaric acid monoester

Preparation analogous to Example 1(a) from 3.7 g. (10 mM) 1,2-O-didecyl-glycerol, 40 ml. chloroform, 2.5 ml. pyridine and 1.8 g. (15.8 mM) glutaric acid anhydride.

TLC $R_f$: 0.77 (ethyl acetate/hexane 1:2 v/v).

1,2-O-Didecyl-rac-glycero-3-glutaric acid resorufin ester (b) Preparation analogous to Example 1(b) from 2.5 g. (5 mM) 5(a), 50 ml. chloroform and 2.2 ml. oxalyl chloride.

(c) Preparation analogous to Example 2(c) from 1.1 g. (5 mM) resorufin, 1 ml. 1,8-diazabicyclo-(5,4,0)-undec-7-ene and 5(b).

TLC $R_f$=0.70 (ethyl acetate/hexane 1:1 v/v).

EXAMPLE 6

(a) 1,2-O-Diundecyl-rac-glycero-3-glutaric acid monoester

Preparation analogous to Example 1(a) from 2 g. (5 mM) 1,2-O-diundecylglycerol, 25 ml. chloroform, 1.4 ml. pyridine and 0.9 g. (7.5 mM) glutaric acid anhydride.

TLC $R_f$: 0.55 (ethyl acetate/petroleum ether 1:2 v/v).
IR (cm$^{-1}$): (film) 1740, 1710

1,2-O-Diundecyl-rac-glycero-3-glutaric acid resorufin ester (b) Preparation analogous to Example 1(b) from 2 g. (3.9 mM) 6(a), 5 ml. chloroform and 1.8 ml. oxalyl chloride.

(c) Preparation analogous to Example 2 (c) from 0.83 g. (3.9 mM) resorufin, 0.61 ml. 1,8-diazabicyclo-(5,4,0)-undec-7-ene and 6(b).

TLC: $R_f$: 0.47 (RP 18, ethanol/acetone 2:1 v/v).

EXAMPLE 7

(a) 1,2-O-Dilauryl-rac-glycero-3-glutaric acid monoester

Preparation analogous to Example 1(a) from 10.7 g. (25 mM) 1,2-O-dilaurylglycerol, 70 ml. chloroform, 5.5 ml. pyridine and 3.3 g. (29 mM) glutaric acid anhydride.

TLC: $R_f$: 0.33 (ethyl acetate/petroleum ether 1:1 v/v).

IR (cm$^{-1}$): (film) 1741, 1708.

1,2-O-Dilauryl-rac-glycero-3-glutaric acid resorufin ester (b) Preparation analogous to Example 1(b) from 5.5 g. (10 mM) 7(a), 50 ml. chloroform and 4.3 ml. oxalyl chloride.

(c) Preparation analogous to Example 2(c) from 2.2 g. (10 mM) resorufin, 100 ml. chloroform, 1.5 ml. 1,8-diazabicyclo-(5,4,0)-undec-7-ene and 7(b).

TLC: $R_f$: 0.78 (ethyl acetate/petroleum ether 1:1 v/v)
IR (cm$^{-1}$): (film) 1765, 1720

EXAMPLE 8

(a) 1,2-O-Dilauryl-rac-glycero-3-pimelic acid monoester (b) Preparation analogous to Example 1(a) from 8.6 g. (20 mM) 1,2-O-dilaurylglycerol, 50 ml. chloroform, 15 ml. pyridine and 4.3 g. (30 mM) pimelic acid anhydride.

TLC: $R_f$: 0.5 (ethyl acetate/petroleum ether 1:2 v/v)
IR (cm$^{-1}$: (film): 1740, 1710.

1,2-O-Dilauryl-rac-glycero-3-pimelic acid resorufin ester (b) Preparation analogous to Example 1(b) from 1.66 g. (3 mM) 8(a) and 1.3 ml. oxalyl chloride.

(c) Preparation analogous to Example 2(c) from 0.65 g. (3 mM) resorufin, 30 ml. chloroform, 0.5 ml. 1,8-diazabicyclo-(5,4,0)-undec-7-ene and 8(b).

TLC: $R_f$: 0.75 (ethyl acetate/hexane 1:1 v/v)
IR (cm$^{-1}$): (film): 1768, 1739

EXAMPLE 9

(a) 1,2-O-Ditetradecyl-rac-glycero-3-glutaric acid monoester

Preparation analogous to Example 1(a) from 14.6 g. (30 mM) 1,2-O-ditetradecylglycerol, 150 ml. chloroform, 8.2 ml. pyridine and 5.1 g. (45 mM) glutaric acid anhydride.

TLC $R_f$: 0.42 (ethyl acetate/petroleum ether 1:2 v/v)
IR (cm$^{-1}$) (KBr) 1740, 1710

1,2-O-Ditetradecyl-rac-glycero-3-glutaric acid resorufin ester (b) Preparation analogous to Example 1(b) from 3 g. (5 mM) 9(a) and 2.2 ml. oxalyl chloride.

(c) Preparation analogous to Example 2(c) from 1.06 g. (5 mM) resorufin, 50 ml. chloroform, 0.75 ml. 1,8-diazabicyclo-(5,4,0)-undec-7-ene and 9(b).

TLC: $R_f$: 0.34 (RP 18, acetonitrile/dichloromethane 1:1 v/v)

IR (cm$^{-1}$): (KBr): 1763, 1735.

EXAMPLE 10

(a) 1,2-O-Ditetradecyl-rac-glycero-3-pimelic acid monoester

Preparation analogous to Example 9(a) from 6.4 g. (45 mM) pimelic acid anhydride.
TLC: $R_f$: 0.45 (ethyl acetate/petroleum ether 1:2 v/v)
IR ($cm^{-1}$) (film) 1740, 1708

1,2-O-Ditetradecyl-rac-glycero-3-pimelic acid resorufin ester (b) Preparation analogous to Example 1(b) from 3.1 g. (5 mM) 10(a) and 2.2 ml. oxalyl chloride.

(c) Preparation analogous to Example 2(c) from 1.06 g. (5 mM) resorufin, 50 ml. chloroform, 0.78 ml. 1,8-diazabicyclo-(5,4,0)-undec-7-ene and 10(b).
TLC: $R_f$: 0.71 (ethyl acetate/petroleum ether 1:2 v/v)
IR ($cm^{-1}$) (film): 1755, 1734.

EXAMPLE 11

(a) 1,2-O-Dihexadecyl-sn-glycero-3-glutaric acid monoester

Preparation analogous to Example 1(a) from 2.7 g. (5 mM) 1,2-O-dihexadecyl-sn-glycerol, 50 ml. chloroform, 3 ml. pyridine and 1.5 g. (13 mM) glutaric acid anhydride.
TLC: $R_f$: 0.65 (ethyl acetate/petroleum ether 1:1 v/v)
IR ($cm^{-1}$) (KBr) 1740, 1710.

1,2-O-Dihexadecyl-sn-glycero-3-glutaric acid resorufin ester (b) Preparation analogous to Example 1(b) from 2.2 g. (3.3 mM) 11(a) and 1 ml. oxalyl chloride.

(c) Preparation analogous to Example 1(c) from 0.71 g. (3.3 mM) resorufin, 20 ml. dimethylformamide, 0.5 ml. pyridine and 11(b).
TLC $R_f$: 0.72 (ethyl acetate/petroleum ether 1:2 v/v).

EXAMPLE 12

(a) 1,2-O-Dibenzyl-rac-glycero-3-glutaric acid monoester

Preparation analogous to Example 1(a) from 3 g. (11 mM) 1,2-O-dibenzylglycerol, 30 ml. chloroform, 2.5 ml. pyridine and 1.8 g. (16 mM) glutaric acid anhydride.
TLC: $R_f$: 0.39 (ethyl acetate/petroleum ether 1:1 v/v +1% glacial acetic acid)

1,2-O-Dibenzyl-rac-glycero-3-glutaric acid resorufin ester (b) Preparation analogous to Example 1(b) from 2.9 g. (7.5 mM) 12(a), 30 ml. chloroform and 3.3 ml. oxalyl chloride.

(c) Preparation analogous to Example 2(c) from 1.6 g. (7.5 mM) resorufin, 75 ml. chloroform, 1.2 ml. 1,8-diazabicyclo-(5,4,0)-undec-7-ene and 12(b).
TLC: $R_f$: 0.48 (ethyl acetate/hexane 1:1 v/v)

EXAMPLE 13

(a) 1-O-Octadecyl-2-O-benzyl-sn-glycero-3-glutaric acid monoester

Preparation analogous to Example 1(a) from 2.2 g. (5 mMole) 1-O-octadecyl-2-O-benzyl-sn-glycerol, 50 ml. chloroform, 3 ml. pyridine and 1.5 g. (13 mM) glutaric acid anhydride. IR ($cm^{-1}$): (film) 1730, 1700.

1-O-Octadecyl-2-O-benzyl-sn-glycero-3-glutaric acid resorufin ester (b) Preparation analogous to Example 1(b) from 1.7 g. (3.1 mM) 13(a) and 1.3 ml. oxalyl chloride.

(c) Preparation analogous to Example 1(c) from 0.8 g. (37 mM) resorufin, 20 ml. dimethylformamide, 0.7 ml. pyridine and 13(b).
TLC: $R_f$: 0.68 (ethyl acetate/petroleum ether 1:1 v/v).
IR ($cm^{-1}$) (KBr): 1768, 1739.

EXAMPLE 14

(a) 1,2-Dioctanoyl-sn-glycero-3-glutaric acid monoester

Preparation analogous to Example 1(a) from 6.8 g. (20 mM) 1,2-dioctanoyl-sn-glycerol, 100 ml. chloroform, 12.5 ml. pyridine and 5.8 g. (50 mM) glutaric acid anhydride.
TLC: $R_f$: 0.49 (ethyl acetate/petroleum ether 1:1 v/v).

1,2-Dioctanoyl-sn-glycero-3-glutaric acid resorufin ester (b) Preparation analogous to Example 1(b) from 2.2 g. (5 mM) 14(a) and 2.2 ml. oxalyl chloride.

(c) Preparation analogous to Example 1(c) from 1.05 g. (5 mM) resorufin, 30 ml. dimethylformamide, 0.75 ml. pyridine and 14(b).
TLC: $R_f$: 0.86 (RP 18, acetonitrile/dichloromethane 1:2 v/v).

EXAMPLE 15

(a) 1,2-Dioleyl-rac-glycero-3-glutaric acid monoester

Preparation analogous to Example 1(a) from 3.1 g. (5 mMole) diolein, 40 ml. chloroform, 3 ml. pyridine and 1.5 g. (13 mM) glutaric acid anhydride.
TLC: $R_f$: 0.32 (ethyl acetate/petroleum ether 1:1 v/v)
IR ($cm^{-1}$) (film): 1740, 1706.

Diolein can be prepared in pure form from technical diolein by column chromatography on silica gel with the use of ethyl acetate/petroleum ether (1:3 v/v) as elution agent.

1,2-Dioleyl-rac-glycero-3-glutaric acid resorufin ester (b) Preparation analogous to Example 1(b) from 3.5 g. (4.8 mM) 15(a) and 1.3 ml. oxalyl chloride.

(c) Preparation analogous to Example 1(c) from 0.9 g. (4.2 mM) resorufin, 20 ml. dimethylfomamide, 1 ml. pyridine and 15(b).
TLC $R_f$: 0.78 (ethyl acetate/petroleum ether 1:1 v/v).

EXAMPLE 16

1,2-O-Ditetradecyl-rac-glycero-3-pimelic acid naphthyl ester

The preparation takes place analogously to Example 10(b) and (c) from 0.72 g. (5 mM) 1-naphthol. Purification by flash chromatography on silica gel with the elution agent ethyl acetate/hexane (1:3 v/v).
TLC: $R_f$: 0.89 (ethyl acetate/petroleum ether 1:5 v/v).

EXAMPLE 17

1,2-Dioleyl-rac-glycero-3-glutaric acid resorufin ester 10.3 g. (14.2 mM) 1,2-Dioleyl-3-glyceroglutaric acid monoester according to Example 15(a), 3.2 g. (15 mM) resorufin, 6.2 g. (30 mM) dicyclohexylcarbodiimide and a spatula tip of 4-dimethylaminopyridine are stirred in 75 ml. dimethylformamide for 2 to 3 days at ambient temperature. The reaction mixture is then diluted with ethyl acetate and the precipitate is filtered off. The ethyl acetate phase is shaken out with 1N hydrochloric acid and dried over anhydrous sodium sulphate. After distilling off the solvent, an oily residue is obtained which is purified by silica gel column chromatography (elution agent: ethyl acetate/petroleum ether 1:1 v/v).

The corresponding chlorophenol red derivative is prepared in the same way.

TLC: $R_f$: 0.69 (RP 18, isopropanol/methanol 1:2 v/v).

EXAMPLE 18

Preparation of 1,2-O-dioctyl-3-pimelic acid monoester

1st step:
Literature: J. H. Short, U. Biermacher, Chim. Ther., 1966, 456; synthesis of pimelic acid monobenzyl ester.

2nd step:
analogously to Example 1(b) from 2.5 g. (10 mM) pimelic acid monobenzyl ester. The oil obtained is added dropwise to a solution of 3.2 g. (10 mM) 1,2-O-dioctylglycerol in 7 ml. pyridine. Working up analogously to Example 1(c).

3rd step:
The above product is dissolved in 20 ml. tetrahydrofuran and, after the addition of 0.4 g. palladium/active charcoal, is hydrogenated. The crude product is purified over a silica gel column. Elution agent: ethyl acetate/petroleum ether (1:1 v/v).

TLC: $R_f$=0.61 (ethyl acetate/petroleum ether 1:1 v/v).

IR (cm$^{-1}$): (film) 1740, 1710.

EXAMPLE 19

Synthesis of 1,2-dioleylglycero-3-glutaric acid monoester (a) 1,2-O-Isopropylideneglycero-3-glutaric acid trichloroethyl ester Step 1:
5.55 g. (42 mM) Isopropylideneglycerol and 12 g. (45.3 mM) 2,2,2-trichloroethyl hydrogen glutarate are dissolved in ethylene glycol dimethyl ether and mixed with 10.5 g. (51 mM) dicyclohexylcarbodiimide. After stirring for two days, the reaction mixture is filtered and the filtrate is distilled; b.p. 170° C./0.1 mm.Hg, colourless oil.

TLC: $R_f$=0.82 (acetone/chloroform 1:8 v/v).

Step 2:
The oil obtained is dissolved in 11 ml. diethyl ether, mixed with 3 ml. methanol and 3 ml. 3N hydrochloric acid and stirred for 12 hours at ambient temperature. The organic phase is shaken with a saturated aqueous sodium hydrogen carbonate solution, then with a saturated aqueous sodium chloride solution and dried. After stripping off the solvent, an oily residue is obtained.

TLC: $R_f$=0.23 (ethyl acetate/petroleum ether 1:1 v/v).

(b) 1,2-Dioleylglycero-3-glutaric acid trichloroethyl ester

Step 3:
6.1 g. (18 mM) of the above-obtained product and 7.84 g. (38 mM) oleic acid are dissolved in 100 ml. ethylene glycol dimethyl ether and a solution of 10.5 g. (37 mM) dicyclohexylcarbodiimide in 50 ml. ethylene glycol dimethyl ether is added dropwise thereto. After stirring for 12 hours at ambient temperature, the reaction mixture is filtered and successively shaken with 3N hydrochloric acid, aqueous sodium hydrogen carbonate solution and then with water. After drying and evaporating the organic phase, the residue is chromatographed on silica gel.

Step 4:
1,2-Dioleylglycero-3-glutaric acid monoester
The trichloroethyl protective group is split off in the manner described in the literature (Juste, Synthesis, 1976, 457).

EXAMPLE 20

(a) 1,2-O-Didecyl-rac-glycero-3-pimelic acid monoester

Preparation analogous to Example 1(a) from 5.6 g. (15 mM) 1,2-O-didecylglycerol, 100 ml. chloroform, 3.2 ml. pyridine and 4.0 g. (28 mM) pimelic acid anhydride.

TLC: $R_f$=0.36 (ethyl acetate/hexane 1:1 v/v).

IR (cm$^{-1}$): (film) 1735, 1710.

1,2-O-Didecyl-rac-glycero-3-pimelic acid resorufin ester (b) Preparation analogous to Example 1(b) from 3 g. (5.8 mM) 20 (a), 50 ml. chloroform and 2.2 ml. oxalyl chloride.

(c) Preparation analogous to Example 2(c) from 1.1 g. (5 mM) resorufin, 1 ml. (6.4 mM) 1,8-diazabicyclo-(5,4,O)-undec-7-ene and 20(b).

TLC: $R_f$=0.71 (ethyl acetate/hexane 1:1 v/v).

IR (cm$^{-1}$): (film) 1755, 1720.

EXAMPLE 21

(a) 1,2-O-Dilauryl-rac-glycero-3-azelaic acid monoester

Preparation analogous to Example 1(a) from 6.7 g. (15.6 mM) 1,2-O-dilaurylglycerol, 100 ml. chloroform, 3.2 ml. pyridine and 4.0 g. (23 mM) azelaic acid anhydride.

TLC: $R_f$=0.22 (ethyl acetate/hexane 1:1 v/v).

IR (cm$^{-1}$): (film) 1738, 1710.

1,2-O-Dilauryl-rac-glycero-3-azelaic acid resorufin ester (b) Preparation analogous to Example 1(b) from 1.5 g. (2.5 mM) 21(a), 30 ml. chloroform and 1.5 ml. oxalyl chloride.

(c) Preparation analogous to Example 2(c) from 0.55 g. (2.5 mM) resorufin, 25 ml. chloroform, 0.5 ml. (3.2 mM) 1,8-diazabicyclo-(5,4,O)-undec-7-ene and 21(b).

TLC: $R_f$=0.78 (ethyl acetate/hexane 1:1 v/v).

IR (cm$^{-1}$): (film) 1762, 1740.

EXAMPLE 22

1.2 g. Sodium desoxycholate and 0.15 mg. colipase (from the pig) are dissolved in 60 ml. distilled water, with stirring. A solution of 70 mg. of the lipase substrate 1,2-O-dioctyl-rac-glycero-3-azelaic acid resorufin ester (Example 4) in 1.7 ml. n-propanol are injected herein under pressure in the thinnest possible stream, with vigorous stirring. A solution which, in 200 ml. distilled water, contains 1.5 g. urea, 1 g. sodium desoxycholate, 200 mg. sodium chloride, 800 mg. TRIS and 107 mg. TRIS.HCl, is well mixed with the above-produced emulsion.

2.5 ml. of the so produced solution are mixed with 100 μl of sample (serum). The reaction is monitored photometrically at 578 nm Hg.

In the case of evaluation via a standard of known lipase activity, the lipase activity of the sample is calculated as follows:

$$\text{activity}_{(sample)} = \frac{\text{activity}_{(standard)} \cdot \Delta E/\text{min (sample)}}{\Delta E/\text{min (standard)}}$$

A calculation of the lipase activity of the sample can also be carried out according to the following equation:

$$\text{activity (sample) } [U/l] = 1000 \cdot \frac{V_{ges}}{\epsilon \cdot V_{sample} \cdot d} \cdot \Delta E/\text{min}$$

$V_{ges}$ = total volume of the test batch [cm$^3$]
$V_{sample}$ = volume of the sample [cm$^3$]
$\epsilon$ = extinction coefficient of the chromogen at 578 nm
$d$ = layer thickness of the cuvette [cm]
$\Delta E/\text{min}$ = extinction change per minute at 578 nm.

In the case of the mentioned reaction conditions, the extinction coefficient $\epsilon = 60.65$ cm·μmol$^{-1}$.

EXAMPLE 23

For various lipase substrates, there were determined blank change, esterase sensitivity, lipase sensitivity and correlation to a turbidimetric turbidity test.

The blank change was determined with a reagent according to Example 1 and various lipase substrates. Instead of the sample, 100 μl. water were added and the extinction change monitored photometrically at 578 nm (ΔmE/min.).

For the determination of the esterase sensitivity, instead of the sample there were added 100 μl. carboxyl esterase (EC 3.1.1.1; about 20,000 U/l. Boehringer Mannheim GmbH, Order No. 10 46 98) and the extinction change monitored as described above.

For the determination of the lipase sensitivity, instead of the sample there were added 100 μl. lipase (EC 3.1.1.3; about 100 U/l., Boehringer Mannheim GmbH, Order No. 41 45 90) and the extinction change monitored as described above.

For the determination of the correlation to a turbidimetric turbidity test, there was carried out a turbidity test (Boehringer Mannheim GmbH, Order No. 26 23 58) with increasing amounts of lipase (0–1000 U/l ), compared with a colour test according to Example 22 and the correlation coefficient determined.

The following Table I summarises the results obtained:

TABLE I

| Example | blank [ΔmE/min] | esterase sensitivity (activity 20,000 U/l) [ΔmE/min] | lipase sensitivity (activity 100 U/l) [ΔmE/min] | correlation coefficient |
|---|---|---|---|---|
| 1 | 13.2 | >1000 | — | — |
| 2 | 7.0 | 144.0 | ~100 | not determined |
| 3 | 3.9–4.1 | 112.5 | 12.28 | 0.9639 |
| 4 | 0.4–0.8 | 33.6 | 18.04 | 0.9421 |
| 5 | 2.4–3.0 | 30.2 | 22.18 | 0.9815 |
| 6 | 2.0–2.8 | 23.6 | 6.96 | 0.9179 |
| 7 | 2.4–3.0 | 34.8 | 10.9 | 0.9636 |
| 8 | 2.1–2.4 | 27.8 | 4.68 | 0.9286 |
| 11 | 0.1 | 1.8 | 0.97 | 0.9830 |
| 20 | 1.3–2.0 | 48.7 | 9.8 | 0.9888 |
| 21 | 9.8–11.9 | 9.5 | 13.2 | 0.9716 |

EXAMPLE 24

8.5 g. Sodium desoxycholate, 0.05 g. colipase, 20 g. mannitol, 0.05 g. calcium chloride, 0.82 g. sodium chloride, 2.7 g. TRIS and 0.4 g. TRIS.HCl are dissolved in 200 ml. distilled water. A solution which contains 0.35 g. 1,2-O-ditetradecyl-rac-glycero-3-pimelic acid naphthol ester in 7 ml. propanol is injected in, with stirring. The emulsion so obtained is frozen at −40° C. and lyophilised.

70 mg. of the lyophilisate obtained are dissolved in 2 ml. distilled water and mixed with 100 μl. of a True Red solution (True Red=4-chloro-3-methylbenzenediazonium-naphthalene-1,5-disulphonate) (231 mg. in 10 ml. distilled water).

After the addition of 100 μl. of sample (serum), the reaction is monitored photometrically at 405 nm.

The determination of the lipase concentration takes place via a calibration curve analogously to Example 22.

EXAMPLE 25

Into a solution of 3.04 g. taurodesoxycholate, 2.7 g. polywax 4000, 7 mg. calcium chloride, 0.2 mg. colipase (from pig) in 120 ml. distilled water are injected, with stirring, 150 mg. of the lipase substrate 1,2-O-didecyl-rac-glycero-3-glutaric acid resorufin ester in 3.5 ml. n-propanol. To the emulsion so obtained is added the following solution and well mixed:

10 g. Taurodesoxycholate, 6.4 g. polywax, 50 g. mannitol, 14 g. urea, 800 mg. sodium chloride and 15 g. Tris are dissolved in 300 ml. distilled water. The pH value is adjusted to 7.5 with a hydrochloric acid solution. Thereafter, the solution is made up to 400 ml. with distilled water.

2.5 ml. of the so produced reaction mixture are mixed with 100 μl. sample (serum) and the reaction is monitored photometrically at 578 nm. The evaluation is carried out as in Example 22.

EXAMPLE 26

Into a solution of 3.04 g. taurodesoxycholate, 2.7 g. polywax 4000, 7 mg. calcium chloride and 0.2 mg. colipase (from pig) in 120 ml. distilled water are injected, with stirring, 150 mg. of the lipase substrate 1,2-O-didecyl-rac-glycero-3-glutaric acid resorufin ester in 3.5 ml. n-propanol. The following solution is added to the emulsion so obtained and well mixed:

10 g. Taurodesoxycholate, 6.4 g. polywax, 50 g. mannitol, 14 g. urea, 800 mg. sodium chloride and 28 g. CHES are dissolved in 300 ml. distilled water. The pH value is adjusted to 8.5 with a hydrochloric acid solution. Thereafter, the solution is made up to 400 ml. with distilled water.

2.5 ml. of the so produced reaction mixture are mixed with 100 μl. sample (serum) and the reaction is monitored photometrically at 578 nm. The evaluation is carried out as in Example 22.

EXAMPLE 27

Into a solution of 4.0 g. sodium taurodesoxycholate, 0.06 g. calcium chloride, 0.2 mg. colipase (from pig), 5.0 g. mannitol and 2.0 g. polywax 4000 in 100 ml. distilled water is injected, with stirring, 150 ml. 1,2-O-ditetradecyl-rac-glycero-3-pimelic acid naphthol ester, which is dissolved in 4 ml. n-propanol. The so obtained emulsion is treated for a few minutes with ultrasonics, with good cooling.

A second solution is prepared containing, in 100 ml., 2.4 g. sodium taurodesoxycholate, 2.0 g. TRIS, 12.0 g. mannitol, 3.5 g. urea and 0.5 g. sodium chloride. The pH value of this solution is adjusted to 8.3 with hydrochloric acid.

A third solution is prepared containing 1 g. True Red (True Red=4-chloro-3-methylbenzenediazoniumnaphthalene-1,5-disulphonate) dissolved in 40 ml. distilled water.

6 Parts of solution 1 and 6 parts of solution 2 are mixed with 1 part of solution 3. The so obtained solution is used to impregnate an absorbent paper suitable for test strip production, for example of the type VS 532 of the firm Schleicher and Schull, and gently dried in a circulating air cabinet at a temperature of from 30° to 65° C.

Until further use, it is recommended to store the impregnated paper in the presence of a moisture-removing agent.

For the testing of the lipase content of a sample (serum), a small amount (few drops) of the sample material is applied to the strip. From the chronological course of the yellow coloration there can be deduced the lipase activity of the sample to be investigated.

EXAMPLE 28

(a)
1,2-O-Dilauryl-rac-glycero-3-tetradecandiacidmonoester

Preparation analogous to example 1(a) from 8.6 g (20 mM) 1,2-O-dilaurylglycerol, 100 ml chloroform, 4 ml pyridine, 0.4 g dimethylaminopyridine, 9.6 g (40 mM) tetradecandiacidanhydride.

TLC: $R_f=0.45$ (ethyl acetate/petroleum ether 1:5)

1,2-O-Dilauryl-rac-glycero-3-tetradecandiacid (6-methylresorufin) ester (b) Preparation analogous to Example 1(b) from 3.35 g (5 mM) 28(a) and 2.2 ml oxalylchloride.

(c) Preparation analogous to Example 2(c) from 1.2 g (5 mM) 4-methylresorufin, 20 ml chloroform, 0.75 ml 1,8-diazabicyclo-(5,4,O)-undec-7-ene, 0.1 g dimethylaminopyridine and 28(b).

TLC: $R_f=0.63$ (ethyl acetate/hexane 1:4)

(d) As stated in Example 22, an emulsion is prepared, with the proviso, that in place of the in Example 22 used lipase substrate a solution of 70 mg of the lipase substrate 1,2-O-dilauryl-rac-glycero-3-tetradecan-diacid-(6-methylresorufin)-ester, dissolved in 1.7 ml n-propanol is used.

Thereby the following test specific characteristics are obtained (cf. Example 23 and Table I):
Blank: 0.2 mE/min
esterase sensitivity: 0.7 mE/min
Lipase sensitivity: 23.6 mE/min per 100 U/l Correlation coefficient: 0.09509

EXAMPLE 29

1,2-O-Dilauryl-rac-glycero-3-glutaric-acid (6-methyl-resorufin)-ester (a) Preparation analogous to the Examples 7(a)–(c) with 2.3 g (10 mM) 4-methylresorufin.

TLC: $R_f=0.68$ (ethyl acetate/hexane 1:2)

(b) Under stirring 0.9 g sodium-taurodesoxycholate and 0.3 g colipase (from pig) are dissolved in 60 ml distilled water. A solution of 70 mg 1,2-O-dilauryl-rac-glycero-3-glutaric acid-(6-methyl-resorufin)-ester in 1.7 ml n-propanol are injected herein under vigorous stirring. To this a solution (200 ml) is added, which contains in 200 ml 0.5 g urea, 1 g sodium-taurodesoxycholate, 200 mg sodium chloride and 2.9 g TRIS, and the pH-value of which is brought at 7.5. After efficient mixing to 2.5 ml of the such prepared solution 100 μl. sample (serum) are added.

The reaction is monitored photometrically at 578 nmHg, and is evaluated as described in Example 22.

Test specific characteristics (cf. Example 23 and Table I):
Blank: 0.4 mE/min
Lipase sensitivity: 28 mE/min per 100 mE/min
Correlation coefficient: 0.988

EXAMPLE 30

4-Methylresorufin

Preparation as described in DE-PS No. 34 11 574 from 7.5 g 2-methyl-4-nitrosoresorcin, 4.2 g resorcin, 3.6 g brown stone, 4.3 ml sulfuric acid, 75 ml methanol, 4 g zinc powder and 18 ml 25% ammonia.

TLC: $R_f=0.70$ (ethanol/acetone 2:1)

UV/VIS (0.1 M potassium phosphate-buffer pH 8.5): max=579 nm

The preparation of 2-methyl-nitrosoresorcin is carried out according to DE-A-No. 34 11 574.

EXAMPLE 31

1,2-0-Dilauryl-rac-glycero-3-glutaric acid-(4-methylumbelliferyl)-ester (a) 2.75 g (5 mM) 7a and 1 g (5 mM) 4-methylumbelliferone are dissolved in 30 ml tetrahydrofuran, and then 2 g (10 mM) dicyclohexylcarbodiimide and 0.15 g dimethylaminopyridine are added. After 24 hours stirring at room temperature filtration and concentration are carried out. The crude material is purified by flash-chromatography.

TCL: $R_f=0.40$ (ethyl acetate/petroleum ether 1:3)

(b) The preparation of the emulsion is carried out as described in Example 22, with the proviso, that in place of the lipase substrate used in this example 35 mg 1,2-dilauryl-rac-glycero-3-glutaric acid-(4-methylumbelliferyl)-ester, dissolved in 1.7 ml n-propanol, are used.

The reaction is monitored fluorometric by 25° C., at an excitation wave length of 364 nm, width of slit 5 nm, and at an emitting wave length of 448 nm and a width of slit of 10 nm.

Test specific characteristics (cf. Example 23 and Table I):
Blank: 0.4 mE/min
Lipase sensitivity: 28 mE/min per 100 U/l
Correlation coefficient: 0.9942

EXAMPLE 32

1,2-O-Dilauryl-rac-glycero-3-glutaric acid-(p-nitrothiophenyl)-ester

Preparation of 32(a)–(b) analogous Examples 7(a)–(b)

(c) Preparation analogous to Example 1(c) from 1.4 g (10 mM) p-nitrothiophenol, 100 ml dimethylformamide, 2.4 ml pyridine, 0.2 g dimethylaminopyridine and 32(b).

TLC: $R_f$=0.76 (ethyl acetate/hexane 1:4).

(d) The following compounds are dissolved under vigorous stirring in 27 ml of distilled water:
4.83 mg sodium desoxycholate
28.00 mg CHES (=2-(cyclohexylamino)-ethanzsulfonic acid)
17.50 g urea
2.13 mg sodium chloride
0.16 mg colipase of pig
0.33 mg calcium chloride
152.00 mg sodium taurodesoxycholate The pH-value of the solution is brought at pH=8.3. To this solution under vigorous stirring a solution of 1,2-O-dilauryl-rac-glycero-3-glutaric acid-(p-nitrothiophenyl)ester is injected. Afterwards the solution is treated with ultrasonics (medium intensity) under cooling for 2 minutes.

To 1 ml of the such prepared emulsion solution 50 μl sample (lipase containing human serum) are added and mixing is carried out. The reaction is monitored photometrically at 405 nm Hg, and is evaluated as described in Example 22. Test specific characteristics:
Blank: 0.3 mE/min
Lipase sensitivity: 12.2 mE/min per 100 U/l
Correlation coefficient: 0.998

EXAMPLE 33

(a)

1-O-(2-Methoxy-octadecyl)-2-O-methyl-rac-glycero-3-glutaric acid monoester

Preparation analogous to Example 1(a) from 3 g (7.7 mM) 1-O-(2-methoxy-octadecyl)-2-O-methyl-glycerol, 25 ml chloroform, 1.8 ml pyridine, 0.1 g dimethylaminopyridine and 1.75 (15 mM) glutaric acid anhydride.

Yield: 1.5 g (39%)
TLC: $R_f$=0.68 (RP18, Acetone/Ethanol 1:2)

1-O-(2-Methoxy-octadecyl)-2-O-methyl-rac-glycero-3-glutaric acid-(6-methyl resorufin) ester (b) Preparation analogous to Example 1(b) from 1.5 g (3 mM) 33(a) and 1.5 ml oxalyl chloride.

(c) Preparation analogous Example 2(c) from 0.68 g (3 mM) 4-methyl resorufin, 0.45 ml 1,8-diazabicyclo-(5,4,0)-undecen-7-ene and 33(b).

TLC: $R_f$=0.86 (ethyl acetate).

(d) The preparation of the test emulsion is carried out as described in Example 22, with the proviso, that as the lipase substrate 1-O-(2-methoxy-octadecyl)-2-O-methyl-rac-glycero-3-glutaric acid (6-methyl-resorufin) ester are used.

The determination of the lipase concentration is made by using a standard straight line from two standards of different lipase concentration, which results from plotting the change of extinction per minute vs. the change of extinction.
Blank: 8.4 mE/min
Esterase sensitivity: 25.3 mE/min
Lipase sensitivity: 19.0 mE/min per 100 U/l
Correlation coefficient: 0.9483

EXAMPLE 34

(a) 1,2-O-Dilauryl-rac-glycero-3-succinic acid monoester

Preparation analogous to Example 1(a) from 8.56 g (20 mM) 1,2-O-dilauryl-glycerol, 4 g (40 mM) succinic acid anhydride, 60 ml chloroform, 4.6 ml pyridine and 0.24 g dimethylaminopyridine. The product crystallizes from hexane.

Fp: 41° to 43° C.
TLC: Rhd f=0.26 (ethyl acetate hexane 1:4)

1,2-O-Dilauryl-rac-glycero-3-succinic acid resorufin ester (b) Preparation analogous to Example 17 from 2.65 g (5 mM) 34(a), 1.06 g (5 mM) resorufin, 6.18 g (30 mM) dicyclohexylcarbodiimide, 0.1 g dimethylaminopyridine and 50 ml dimethylformamide.

TLC: $R_f$=0.47 (ethyl acetate/petroleum ether 1:3).

(c) The emulsion is prepared as described in Example 22, too. But in this case as the lipase substrate 70 mg 1,2-O-dilauryl-rac-glycero-3-succinic acid resorufin ester, dissolved in 1.7 ml propanol, are used.

Thereby the following test specific characteristics are obtained (cf. Example 23 and Table I):
Blank: 3.8 to 4.0 mE/min
Esterase sensitivity: not evaluated
Lipase sensitivity: 8.7 mE/min per 100 U/l
Correlation coefficient: 0.8793.

EXAMPLE 35

(a) 2-O-Lauryl-octadecandiol-(1,2)-1-glutaric acid monoester

Preparation analogous Example 1(a) from 4.6 g (10 mM) 2-O-lauryl-octadecandiol-(1,2), 29 ml chloroform, 2,3 ml pyridine, 0.12 g dimethylaminopyridine, 2.3 g (20 mM) glutaric acid anhydride.

TLC: $R_f$=0.54 (petroleum ether/ ethyl acetate 4:1)

2-O-Lauryl-octandiol-(1,2)-1-glutaric acid-(6-methylresorufin)-ester (b) Preparation analogous Example 1(b) from 1.15 g (2 mM) 35(a) and 0.88 ml oxalyl chloride.

(c) Preparation analogous Example 2(c) from 0.45 g (2 mM) 4-methylresorufin, 20 ml chloroform, 0.3 ml 1,8-diazabicyclo-(5,4,0)-undec-7ene, 40 mg dimethylaminopyridine and 35(b).

TLC: $R_f$=0.37 (petroleum ether/ethyl acetate 5:1)

(d) An emulsion is prepared as stated in Example 22, with the proviso, that as the lipase substrate 70 mg 2-O-lauryl-octadecandiol-(1,2)-1-glutaric acid (6-methylresorufin) ester, dissolved in 1.7 ml n-Propanol, are used.

According to Example 23, table I, the following test specific characteristics are obtained:
Blank: 0.3 to 1.0 mE/min
Esterase sensitivity: 1.0 mE/min
Lipase sensitivity: 25.5 mE/min per 100 U/l
Correlation coefficient: 0.996

EXAMPLE 36

(a) 1,2-O-Dilauryl-rac-3-thioglycero-3-S-glutaric acid monoester

Preparation analogous to Example 1(a) from 2.5 g (4.8 mM) 1,2-O-dilauryl-rac-3-thioglycerol, 14 ml chloroform, 1,1 ml pyridine and 1.1 g (9.6 mM) glutaric acid anhydride.

TLC: $R_f=0.5$ (hexane/tetrahydrofuran 1:4)

1,2-O-Dilauryl-rac-3-thioglycero-3-S-glutaric acid (6-methylresorufin) ester (b) Preparation analogous Example 1(b) from 0.74 g (1.3 mM) 36(a) and 0.6 ml oxalylchloride.

(c) Preparation analogous Example 2(c) from 0.3 g (1.3 mM) 4-methylresorufin, 13 ml chloroform, 0.2 ml 1,8-diazabicyclo-(5,4,0)-undec-7-ene, 27 mg dimethylaminopyridine and 36(b).

TLC: $R_f=0.38$ (petroleum ether/ethyl acetate 17:3)

The 1,2-O-dilauryl-rac-3-thioglycerol, used as the starting material, is obtained analogous to Organic Synthesis III, page 366 and page 363 in the following manner:

Reaction of 1,2-O-dilaurylglycerol and toluol sulfonic acid chloride to the dilauryl-glycero-3-toluolsulfonate, then reaction with thio urea to the corresponding isothiuronium salt, and then hydrolysis with hydrochloric acid.

TLC: $R_f=0.52$ (petroleum ether/ethy acetate 49:1)

(d) An emulsion is prepared according to Example 22. But instead of the lipase substrate used in this example a solution of 70 mg 1,2-O-dilauryl-rac-3-thioglycero-3-S-glutaric acid (6-methylresorufin) ester in 1.7 ml n-propanol is used.

Test specific characteristics:
Blank: 0.2 to 0.9 mE/min
Esterase sensitivity: 1.3 mE/min
Lipase sensitivity: 4.1 mE/min per 100 U/l
Correlation coefficient: 0.857

EXAMPLE 37

(a) 1,2-S-Dilauryl-rac-1,2-dithioglycero-3-glutaric acid monoester

Preparation analogous to Example 1(a) from 3 g (6.5 mM) 1,2-S-dilauryl-1,2-dithioglycerol, 30 ml pyridine and 1.5 g (13 mM) glutaric acid anhydride.

TLC: $R_f=0.43$ (petroleum ether/ethyl acetate 1:1)

1,2-S-Dilauryl-rac-1,2-dithioglycero-3-glutaric acid (6-methylresorufin) ester (b) Preparation analogous Example 1(b) from 1.2 g (2 mM) 3(a) and 1 ml oxalyl chloride.

(c) Preparation analogous Example 2 (c) from 0.46 g (2 mM) 4-methylresorufin, 20 ml chloroform, 0.3 ml 1,8-diazabicyclo-(5,4,0)-undec-7-ene and 37(b).

TLC: $R_f=0.37$ (petroleumether/ethylacetate 4:1)

The 1,2-S-dilauryl-rac-1,2-dithioglycerol, used as the starting material, is prepared in the following manner:

To a solution of 9 g (160 mM) sodium hydroxide in 250 ml ethanol, 10 g (80 mM) 2,3-dimercaptopropanol in 100 ml ethanol are dropped at room temperature. After stirring during 1 hour a solution of 40 g (160 mM) dodecyclbromide in 100 ml ethanol are added dropwise. For the completion of the reaction stirring is continued for further 2 days, then filtrated and the filtrate is mixed with ice. After acidifying with 2N hydrochlorid acid extraction is carried out with ether for three times, the organic phase is dried and concentrated. The residue is purified over a silica gel column (elution agent: ethyl acetate/petroleum ether 1:10). TLC: $R_f=0.54$ (ethyl acetate/petroleum ether 1:10).

(d) An emulsion is prepared as stated in Example 22. Instead of the lipase substrate used in this example in this case 1,2-S-dilauryl-rac-1,2-dithioglycero-3-S-glutaric acid (6-methylresorufin) ester, 70 mg dissolved in 1.7 ml n-propanol, are used.

Blank: 3 mE/min.
Esterase sensivity: 3,4 mE/min.
Lipase sensivity: 24 mE/min.
Correlation coefficient: 0,9943

We claim:

1. A lipase substrate of the formula:

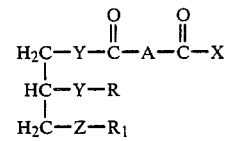

wherein A is an alkylene or alkenylene radical containing up to 16 carbon atoms, R and $R_1$, which can be the same or different, each signify alkyl, alkenyl or acyl containing up to 20 carbon atoms or an optionally alkyl-substituted aryl or aralkyl radical containing up to 8 carbon atoms in the alkyl moiety and wherein one of R and $R_1$ can also be a hydrogen atom, X is an aromatic hydroxy or thiol residue selected from the group consisting of resorufin, chlorophenol red, indoxyl, and thiofluorescein each Y independently from each other, is —S— or —O—, and each Z independently from each other is other is —S—, —O— or —$CH_2$—.

2. The lipase substrate of claim 1, wherein R and/or $R_1$ contain 8 to 12 carbon atoms.

3. The lipase substrate of claim 1, wherein A contains 3 to 7 carbon atoms.

4. 1,2-O-Dioctyl-rac-glycero-3-azelaic acid resorufin ester.

5. 1,2-O-Dioctyl-rac-glycero-3-pimelic acid resorufin ester.

6. 1,2-O-Dioctyl-rac-glycero-3-glutaric acid resorufin ester.

7. 1,2-O-Dioctyl-rac-glycero-3-glutaric acid resorufin ester.

* * * * *

UNITED STATES PATENT AND TRADEMARK OFFICE
CERTIFICATE OF CORRECTION

PATENT NO. : 4,847,376
DATED      : July 11, 1989
INVENTOR(S): Ulrich Neumann, et al.

It is certified that error appears in the above-identified patent and that said Letters Patent is hereby corrected as shown below:

| | |
|---|---|
| Col. 6, line 67: | change "ethyl/petroleum" to -- ethyl acetate/petroleum --. |
| Col. 17, line 13: | change "ethanzsulfonic" to -- ethanesulfonic --. |
| Col. 18, line 12: | change "TLC: Rhd f" to --TLC: $R_f$--. |
| Col. 19, line 23: | change "ethy" to -- ethyl --. |
| Col. 20, lines 49 & 51: | change "Dioctyl" to -- Didecyl --. |
| Col. 20, line 53: | change "Dioctyl" to -- Didodecyl --. |

Signed and Sealed this

Seventh Day of August, 1990

Attest:

HARRY F. MANBECK, JR.

*Attesting Officer*     Commissioner of Patents and Trademarks